United States Patent [19]

Debbas

[11] Patent Number: 5,716,409
[45] Date of Patent: Feb. 10, 1998

[54] REINFORCEMENT SHEET FOR USE IN SURGICAL REPAIR

[76] Inventor: Elie Debbas, 4104 N. Garland St., Alexandria, Va. 20744

[21] Appl. No.: 732,143

[22] Filed: Oct. 16, 1996

[51] Int. Cl.$^6$ ............................................. A61F 2/02
[52] U.S. Cl. ..................... 623/11; 623/12; 623/13; 606/151
[58] Field of Search ........................ 623/1, 11, 12, 623/13; 606/151

[56] References Cited

U.S. PATENT DOCUMENTS

| | | | |
|---|---|---|---|
| 2,671,444 | 12/1954 | Pease, Jr. | 128/82 |
| 4,347,847 | 9/1982 | Usher | 128/334 |
| 4,452,245 | 6/1984 | Usher | 606/151 |
| 4,693,720 | 9/1987 | Scharnberg et al. | 623/11 |
| 4,769,038 | 9/1988 | Bendavid et al. | 623/13 |
| 5,122,155 | 6/1992 | Eberbach | 606/151 |
| 5,147,374 | 9/1992 | Fernandez | 623/12 |
| 5,176,692 | 1/1993 | Wilk et al. | 606/151 |
| 5,290,217 | 3/1994 | Campos | 606/151 |
| 5,356,432 | 10/1994 | Rutkow et al. | 623/1 |
| 5,368,602 | 11/1994 | de la Torre | 606/151 |
| 5,370,650 | 12/1994 | Tovey et al. | 623/11 |
| 5,383,477 | 1/1995 | DeMatteis | 128/898 |
| 5,425,740 | 6/1995 | Hutchinson, Jr. | 606/151 |
| 5,456,720 | 10/1995 | Schultz et al. | 623/12 |

*Primary Examiner*—Michael J. Milano
*Assistant Examiner*—Tram Anh T. Nguyen
*Attorney, Agent, or Firm*—Burns, Doane, Swecker & Mathis, L.L.P.

[57] ABSTRACT

A reinforcement sheet for use in surgery includes an opening, for example to receive the spermatic cord or the round ligament in surgical hernia repair, with the opening defined at an interior of the sheet when the sheet is substantially flat, with the sheet having a first edge which extends from the opening to the perimeter of the sheet and a second edge, which is preferably provided by a flap, with the sheet substantially overlying the first edge of the sheet when the sheet and the flap are generally flat and with the second edge substantially overlying the sheet when the sheet is generally flat.

27 Claims, 3 Drawing Sheets

REINFORCEMENT SHEET FOR USE IN SURGICAL REPAIR

BACKGROUND AND SUMMARY OF THE PRESENT INVENTION

The present invention relates generally to medical devices for use in surgery and more particularly to a mesh for use in surgical hernia repair.

Surgical hernia repair is today one of the most commonly performed surgeries. Unfortunately, surgical hernia repair also is one of the most commonly repeated surgeries either because the initial repair did not adequately reinforce the hernia or because additional strain in the area of the hernia repair results in a breakdown of the repair. Over the years, considerable effort has been directed toward the improvement of surgical hernia repair with a particular goal being the reduction of instances in which surgical hernia repair needs to be repeated.

One way in particular in which surgical hernia repair has been improved is through the use of mesh to reinforce the hernia repair. Various mesh materials are in common use with a mesh known in the trade as Marlex being among the most popular and most commonly used hernia mesh repair materials.

The use of a mesh for surgical hernia repair for male patients involves a complexity, however, because many hernias occur in the vicinity of the spermatic cord. Accordingly, the mesh typically needs to encircle the spermatic cord in order to provide adequate reinforcement throughout the area of the hernia repair which means that the spermatic cord must pass through the mesh material.

The use of a mesh for surgical hernia repair for female patients involves a similar complexity because of the round ligament. In a surgical hernia repair operation on a female patient the mesh must typically encircle the round ligament in order to provide adequate reinforcement throughout the area of the hernia repair. Accordingly, the round ligament typically must pass through the mesh material.

As a result, the mesh material is provided with a suitably sized opening to accommodate the spermatic cord or the round ligament with a cut extending from the opening for the spermatic cord or the round ligament to the edge or perimeter of the mesh material. During the surgery, the surgeon then sutures or staples the mesh in place about the perimeter of the mesh as well as along the cut leading to the spermatic cord or to the round ligament. Positioning the mesh flat with the edges of the cut adjacent to one another is difficult and time consuming and frequently quite difficult to achieve in surgical hernia repair. This procedure is particularly difficult to perform properly in the case of laparoscopic surgical hernia repair.

Laparoscopic surgery in which a sheet of mesh material is used to reinforce the hernia repair is considered to be a significant improvement in surgical hernia repair. Such laparoscopic surgery is now commonplace and enjoys a relatively high level of success.

The adequacy of the surgical hernia repair (whether done through laparoscopic surgery or otherwise) depends upon numerous factors such as whether an adequately sized mesh material has been used, whether the mesh has been positioned and secured in place without wrinkles, and whether there has been an adequate closure of the mesh material about the spermatic cord or the round ligament to avoid having a relatively weakened area in the repair.

In the case of laparoscopic surgical hernia repair, suturing becomes a difficult and tedious task with the result that staples have largely replaced sutures to anchor the mesh to the appropriate anatomical structures. However, the proper positioning and anchoring of the edges of the mesh along the cut leading to the opening for the spermatic cord or the round ligament by stapling in a wrinkle-free manner is particularly difficult, especially in laparoscopic surgery.

Accordingly, it is an object of the present invention to provide a mesh for use in surgical hernia repair which overcomes the problems associated with the proper positioning and anchoring of the mesh.

Another object of the present invention is to provide a mesh which may be easily positioned and anchored about the spermatic cord or the round ligament in laparoscopic surgery.

Yet another object of the present invention is to provide a mesh which may be properly positioned about the spermatic cord or the round ligament in surgical hernia repair in a relatively wrinkle-free manner and anchored in place using staples or sutures.

Still another object of the present invention is to provide a mesh which overcomes the disadvantages of the known mesh configurations for surgical use.

A still further object of the present invention is to provide a mesh having a flap which is anchored to the mesh on one side of a cut and which overlaps the cut in the mesh in order to provide reinforcement in the mesh in the area of the cut.

These and other objects are accomplished by a surgical mesh according to the present invention.

A reinforcement sheet for use in surgery according to the present invention comprises a sheet having an opening defined at an interior of the sheet when the sheet is substantially flat. The sheet has a first edge which extends from the opening to the perimeter of the sheet. The sheet has a second edge with the sheet substantially overlying the first edge of said sheet when the sheet is generally flat and with the second edge substantially overlying the sheet when the sheet is generally flat.

According to a more preferred embodiment of the present invention, a reinforcement sheet of mesh material for use in surgical hernia repair has an opening to receive a body member such as the spermatic cord or the round ligament of the patient. The opening is defined at an interior of the sheet when the sheet is substantially flat. The sheet has a first edge which extends from the opening to the perimeter of the sheet and a second edge which substantially overlies the first edge of the sheet when the sheet is generally flat. The second edge is preferably provided by a flap which is connected to the sheet along one side of the first edge with the flap overlying the first edge when the sheet and flap are substantially flat.

BRIEF DESCRIPTION OF THE DRAWINGS

Preferred embodiments of the present invention will be described in greater detail with reference to the accompanying drawings, wherein like members bear like reference numerals and wherein.

DETAILED DESCRIPTION OF THE PREFERRED EMBODIMENTS

Figure 1:
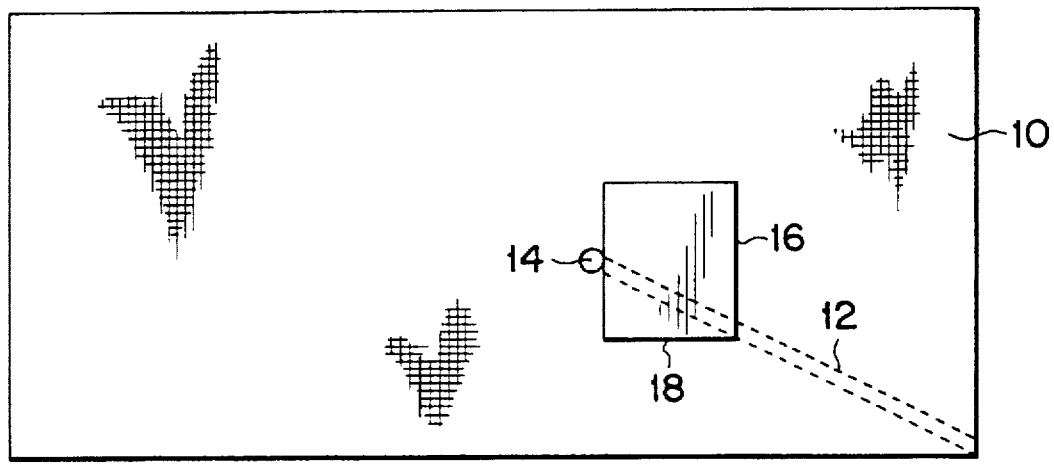
FIG. 1 is a top view of a preferred embodiment of a mesh for surgical hernia repair according to the present invention.

With reference to FIG. 1, a preferred embodiment of a sheet for surgical hernia repair includes a sheet of mesh material 10 such as the surgical mesh material known in the trade as Marlex or another mesh material which is suitable and acceptable for surgical hernia repair. The sheet of mesh material 10 as shown in FIG. 1 is approximately 3 inches by 5 inches although the exact size and shape of the sheet of mesh material may be determined by the surgeon depending upon the particular hernia repair being performed and the age and size of the patient.

Typically, an opening 14 is provided in the sheet of mesh material near but not precisely at the center of the sheet of mesh material 10 to accommodate the spermatic cord or the round ligament of the patient (not shown). The opening 14 may be of any appropriate size with the opening 14 typically being round with a diameter of about 2 to 10 millimeters.

In the case of a right-sided hernia and if the mesh material is approximately 3 inches wide and 5 inches long, the opening 14 may be provided about 2 inches from the right side of the sheet of mesh material 10 (and 3 inches from the left side of the sheet of mesh material 10). In the preferred embodiment as shown in FIG. 1, the opening 14 is provided about 1.75 inches down from the top edge of the sheet of mesh material 10 (and about 1.25 inches up from the bottom edge of the sheet of mesh material 10). In this way, the opening 14 is provided at a location in the sheet of mesh material which is sufficient to provide an ample expanse of mesh material circumferentially about the spermatic cord or about the round ligament.

In order to be able to position the sheet of mesh material about the spermatic cord or the round ligament, the sheet of mesh material must also have a passageway 12 or cut which extends from the opening 14 continuously to the perimeter or outside edge of the sheet of mesh material. The passageway 12 or cut defines a first edge which extends from the opening 14 continuously to the perimeter or outside edge of the sheet of mesh material. In the embodiment of FIG. 1, the passageway 12 or cut also defines a third edge which is substantially parallel to the first edge. In the embodiment of FIG. 1, the passageway 12 extends diagonally from the opening 14 for the spermatic cord or for the round ligament to the right lowermost corner of the sheet of mesh material 10.

The opening 14 for the spermatic cord or for the round ligament as well as the passageway 12 extending from the opening 14 to the edge of the sheet of mesh material 10 may either be provided by the supplier of the mesh material or the passageway 12 and the opening 14 may be made by the surgeon in connection with the hernia repair. In either event, the opening 14 must be sufficiently large to accommodate the spermatic cord or the round ligament but the opening is preferably as small as possible so as to provide the maximum amount of reinforcement for the patient in the area immediately adjacent to the spermatic cord or the round ligament.

The passageway 12 which extends from the opening 14 for the spermatic cord or for the round ligament may simply be a cut through the mesh material so that when the mesh material is flat, the edges of the mesh material on either side of the passageway 12 nearly abut one another. The passageway 12 may also result from the cutting away of a small strip of mesh material such that when the sheet of mesh material 10 is flat there is a slight gap between the adjacent edges of the sheet of mesh material which form the passageway 12.

According to the present invention, the sheet of mesh material 10 is provided with a flap 16 which overlies at least a portion of the passageway 12. The flap 16 defines a second edge which substantially overlies the sheet when the sheet is generally flat. In the preferred embodiment of FIG. 1, the flap 16 is rectangular in shape with the flap initially connected to the sheet of mesh material 10 only on one side of the passageway 12. For example, as shown in the embodiment of FIG. 1, the flap 16 is attached to the sheet 10 along the bottom edge 18 of the flap and along the lower half of the left edge of the flap 16 prior to positioning of the mesh about the spermatic cord or about the round ligament of the patient. Because the flap is initially connected to the sheet of mesh material only on one side of the passageway 12, the flap 16 does not prevent the sheet of mesh material from being positioned about the spermatic cord or the round ligament with the spermatic cord or with the round ligament then received by the opening 14.

The flap 16 may be initially attached to the sheet of mesh material 10 by suturing the flap to the mesh material with sutures or the flap may be stapled to the sheet of mesh material using suitable, conventional staplers for surgical repair. Of course, if provided by the manufacturer or supplier of the mesh 10, the flap may be bonded or welded or fused to the mesh 10 on one side of the passageway 12 in any suitable, conventional manner which will not present problems when the mesh is used in a surgical hernia repair. For example, if the flap 16 is glued to the mesh 10, the adhesive used to connect the flap to the mesh must be biologically inert and not have a propensity to cause the body to reject the use of the mesh in the surgical hernia repair. In addition, the adhesive (or the sutures or the staples) used with the mesh and the flap should be sufficiently strong so as to withstand the strain and stress expected to be encountered by the flap and mesh when reinforcing the area of the hernia in the patient.

With reference to FIG. 1, the flap 16 need not extend along the entire passageway 12. Instead, the mesh 16 preferably overlaps the area of the passageway 12 especially in the area adjacent to the opening 14 so as to provide reinforcement in this area of the hernia repair. For example, in the preferred embodiment of FIG. 1, the flap 16 is approximately ¾ inches wide and 1 inch long with the midpoint of the left edge of the flap overlapping the passageway 12 adjacent to the opening 14.

During surgery, the mesh 10 (with the flap 16 attached to the mesh 10 along one side of the passageway 12) is positioned over the area of the hernia repair in the conventional manner so that the mesh 10 essentially lies flat. In addition, the flap 16 is arranged to overlie the mesh 10 and the passageway 12 with the flap also arranged to lie essentially flat with no wrinkles. The mesh 10 and the flap 16 are then sutured or stapled in place. During the hernia repair surgery, the flap 16 is preferably stapled or sutured in place along the edges of the flap 16.

In each of the embodiments of the present invention care should be given to avoid potential injury to the nerves of the patient during stapling. In this way, it is preferable to arrange the passageway 12 as well as the flap 16 so as to be relatively remote from areas in which the stapling may potentially injure the nerves of the patient.

Figure 2:
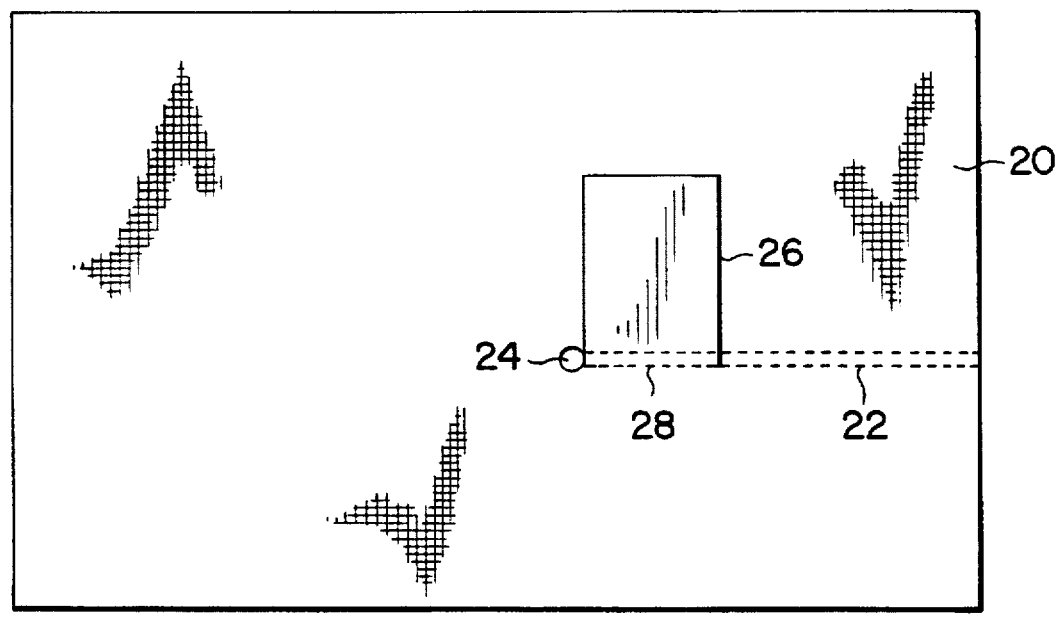
FIG. 2 is a top view of another embodiment of a mesh for surgical hernia repair according to the present invention.

With reference now to FIG. 2, another preferred embodiment of the mesh and flap according to the present invention is shown. In this embodiment, a rectangular sheet of Marlex mesh 20 is provided with a suitably sized opening 24 to accommodate the spermatic cord or the round ligament as explained above in connection with the embodiment of FIG. 1. In the embodiment of FIG. 2, however, a passageway 22 extends from the opening 24 horizontally to the right edge of the sheet. The passageway 22 defines a first edge which extends from the opening 24 continuously to the perimeter or outside edge of the sheet of mesh material. In the embodiment of FIG. 2, the passageway 22 also defines a third edge which is substantially parallel to the first edge. A flap 26 of Marlex or other suitable material is provided with the flap 26 being initially connected along a lowermost edge of the flap 28 to the lowermost edge of the passageway 22. The flap 26 defines a second edge which substantially overlies the sheet when the sheet is generally flat.

In the embodiment of FIG. 2, the flap 26 is again rectangular in shape and has a length of approximately 1 inch and a width of approximately ¾ inches. The flap overlies a portion of the passageway 22 with the leftmost edge of the flap being adjacent to the opening 24 at the lowermost left corner of the flap.

Figure 3:
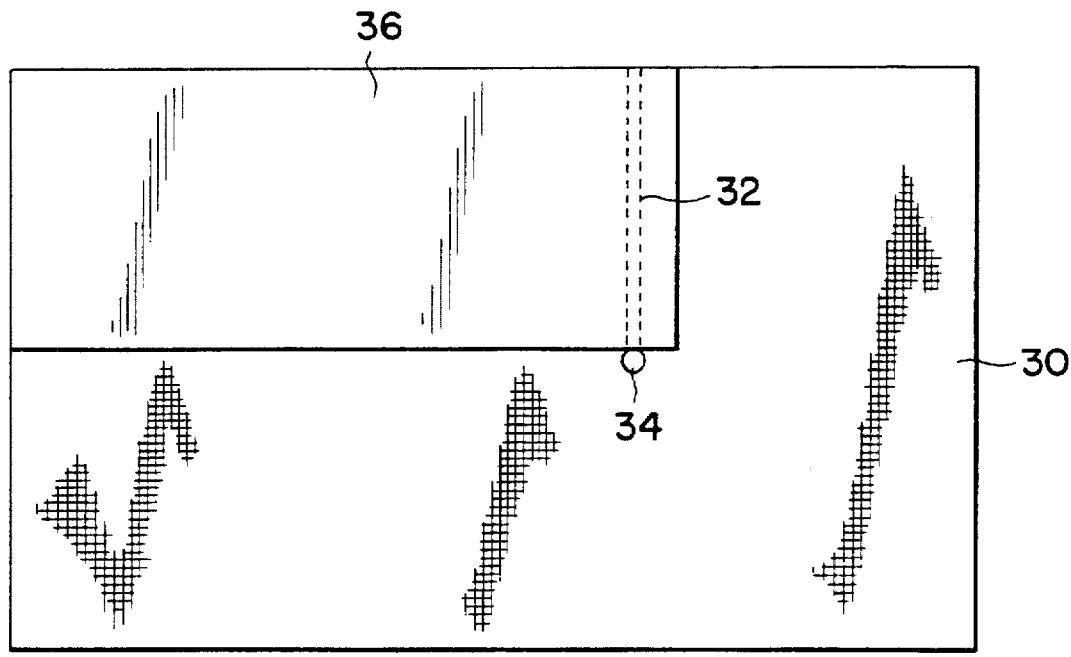
FIG. 3 is a top view of another embodiment of a mesh for surgical hernia repair according to the present invention.

With reference now to FIG. 3, another preferred embodiment of the present invention includes a sheet of mesh material 30 again provided with an opening 34 for the spermatic cord or the round ligament (not shown). In the embodiment of FIG. 3, a passageway 32 extends vertically upwardly from the opening 34 to the top edge of the mesh 30. The passageway 32 defines a first edge which extends from the opening 34 continuously to the perimeter or outside edge of the sheet of mesh material. In the embodiment of FIG. 3, the passageway 32 also defines a third edge which is substantially parallel to the first edge. A flap 36 having a rectangular shape is provided with the right edge of the flap 36 corresponding to the length of the passageway 32. The flap 36 is connected to the mesh along the right edge of the flap on the right side of the passageway 32 either by stapling or by suturing or by another suitable manner as discussed above in connection with the embodiment of FIG. 1.

The left side of the flap 36 extends toward the left edge of the sheet of mesh 30 with the left edge of the flap lying adjacent the left edge of the sheet 30 and the top edge of the flap 36 extending parallel to the top edge of the sheet 30. The bottom edge of the flap 36 extends parallel to the bottom edge of the sheet 30 and lies slightly above the opening 34.

In use, the mesh 30 is positioned over the area to be reinforced with the spermatic cord or the round ligament provided through the opening 34. The mesh 30 is arranged to essentially lie flat without wrinkles and the flap 36 is positioned to overlie the passageway 32. The flap 36 defines a second edge which substantially overlies the sheet when the sheet is generally flat. The mesh 30 is then sutured of stapled in place and the flap 36 is also sutured or stapled in place about the perimeter of the flap 36. This preferred embodiment offers the additional advantage of having a second layer of mesh in the area where the herniae typically occurs.

Figure 4:
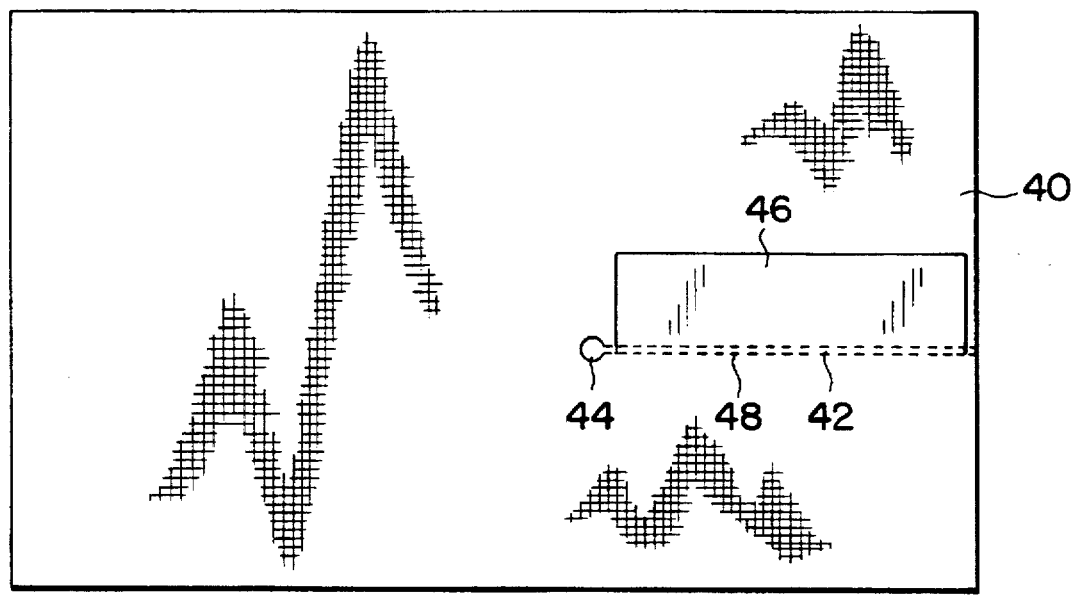
FIG. 4 is a top view of another embodiment of a mesh for surgical hernia repair according to the present invention.

With reference now to FIG. 4, another embodiment of the present invention is shown in which a sheet of mesh material 40 is provided with an opening 44 to receive the spermatic cord or the round ligament (not shown) during a hernia repair. A passageway 42 extends from the opening 44 to the right edge of the mesh 40 with a rectangular flap 46 provided with the mesh. The passageway 42 defines a first edge which extends from the opening 44 continuously to the perimeter or outside edge of the sheet of mesh material. In the embodiment of FIG. 4, the passageway 42 also defines a third edge which is substantially parallel to the first edge. The rectangular flap 46 has a length which corresponds to the length of the passageway 42 with the lowermost edge 48 of the flap 46 being connected to the lowermost edge of the passageway 42 by suturing, stapling, or by any suitable, conventional manner, as described above. The flap 46 has a width of approximately ¾ inches in order to adequately overlie the passageway 42. The flap 46 defines a second edge which substantially overlies the sheet when the sheet is generally flat. In this way, the flap 46 provides reinforcement in the mesh in the area of the passageway 42 and especially adjacent to the opening 44.

According to the present invention, the sheet of mesh material may also have a relatively wide passageway (perhaps a rectangular shape or a triangular shape) which is cut out of the mesh material 10 in order to provide access to the opening which receives the spermatic cord or the round ligament.

Figure 5:
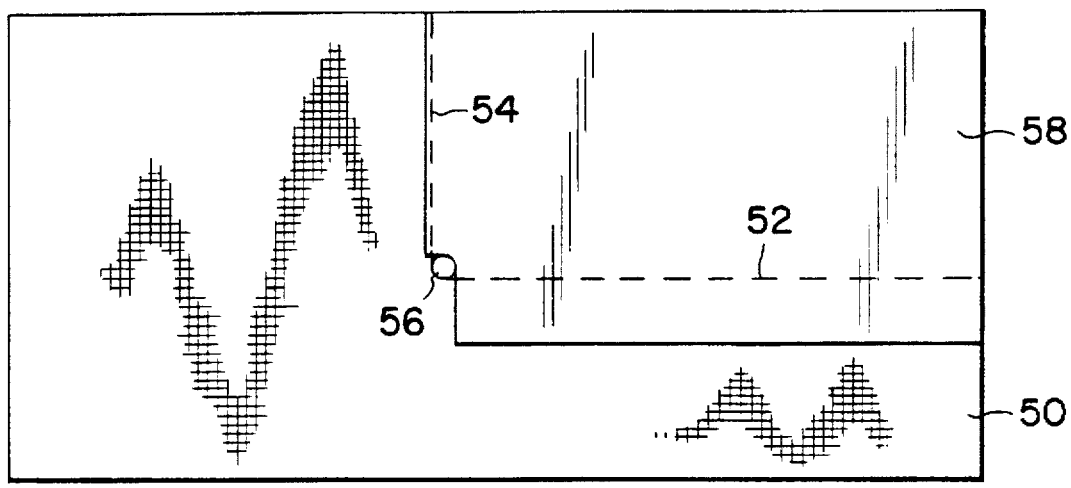
FIG. 5 is a top view of another embodiment of a mesh for surgical hernia repair according to the present invention; and, FIG. 6 is a top view of another embodiment of a mesh for surgical hernia repair according to the present invention.

With reference to FIG. 5, a sheet of mesh material 50, has a generally rectangular shape with a corner of the sheet removed along the cut lines 52 and 54 (shown in phantom). The cut line 52 defines a first edge which extends from the opening 54 continuously to the perimeter or outside edge of the sheet of mesh material. In the embodiment of FIG. 5, the cut line 54 defines a third edge which is at a right angle to the first edge. In addition, an opening 56, comprising a curved cut line in the mesh is provided to receive the spermatic cord or the round ligament. In the embodiment of FIG. 5, a flap 58 is provided which is generally rectangular in shape and sized so as to overlie the mesh along the cut line 52. The flap 58 defines a second edge which substantially overlies the sheet when the sheet is generally flat. The flap 58 has an edge that corresponds generally to the cut line 54 with a lowermost left corner of the flap 58 cut in a curved manner to accommodate the spermatic cord or the round ligament (not shown). The flap 58 is initially connected to the mesh 50 along the cut line 54 of the mesh and along the left edge of the flap 58 either by suturing or by stapling or by another suitable manner as described above. The flap 58 is sized so as to overlie the mesh 50 along the cut line 52. The curved edge of the flap at the lower left corner of the flap cooperates with the curved opening 56 to define a circular opening for the spermatic cord or for the round ligament. In this way, the flap 58 provides a reinforcement for the mesh along the passageway (defined by the cut lines 52 and 54) to receive the spermatic cord or the round ligament.

Figure 6:
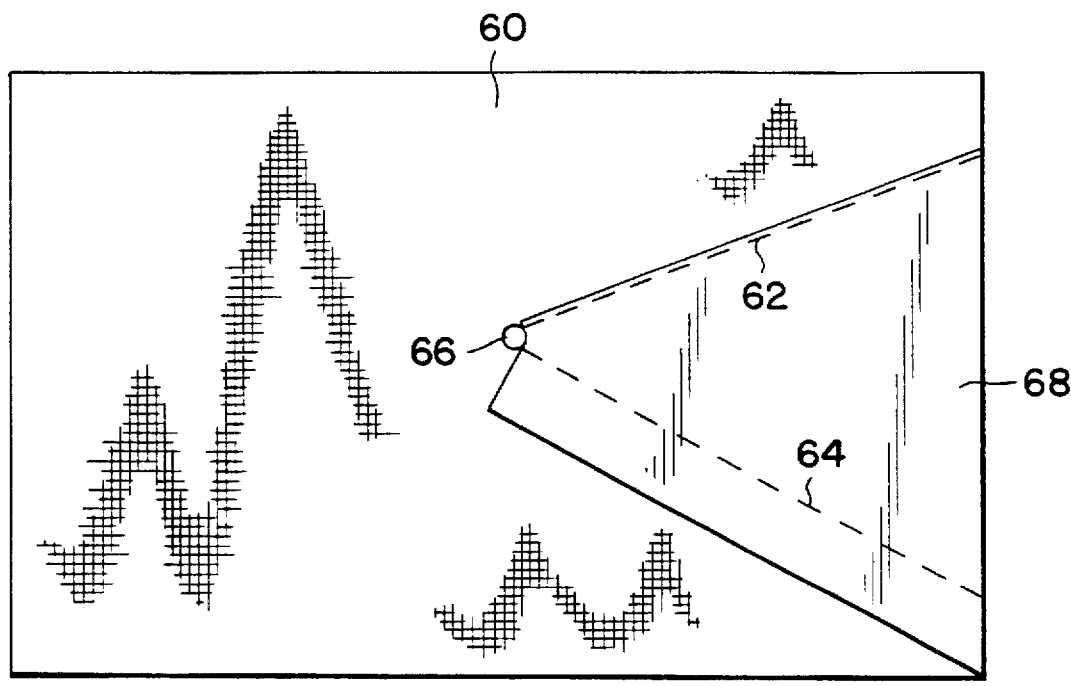

With reference to FIG. 6, a configuration which is similar to that of FIG. 5, is shown in which a sheet of mesh material 60 is provided with a first cut line 62 and a second cut line 64 (shown in phantom) which define a triangular passageway in the mesh 60. The cut line 64 defines a first edge which extends from the opening 66 continuously to the perimeter or outside edge of the sheet of mesh material. In the embodiment of FIG. 6, the cut line 62 defines a third edge which is at an angle to the first edge. The innermost corner defined by the cut lines 62 and 64 is rounded at 66 so as to accommodate the spermatic cord or the round ligament. A flap 68 having a triangular size which generally corresponds to the triangular size of the passageway in the mesh is provided with one edge of the flap being connected to the mesh along the cut line 62. The flap is rounded at the left corner of the flap so as to define the opening for the spermatic cord or for the round ligament together with the rounded cut line 66. The flap 68 overlies the other cut line 64 of the mesh so as to provide reinforcement in the vicinity of the passageway for the spermatic cord or for the round ligament and along the cut line 64. The flap 68 defines a second edge which substantially overlies the sheet when the sheet is generally flat.

In use, the mesh 60 is positioned about the spermatic cord or about the round ligament with the mesh 60 and the flap 68 substantially flat and wrinkle-free. The mesh and flap are then sutured or stapled in place so as to reinforce the area of the hernia, especially about the spermatic cord or about the round ligament.

Of course, in the present invention, the flap may be formed integrally in the mesh material so that when the mesh is flat and substantially wrinkle-free, the integral "flap" overlies the passageway provided to enable the mesh to receive the spermatic cord or the round ligament at an interior location in the mesh.

While the present invention has been described with reference to the preferred embodiments described herein in connection with surgical hernia repair, it is expected that the mesh and flap arrangement may be of general utility in surgery, especially whenever a mesh is used in order to provide reinforcement about a vessel or other member which is connected at both ends. In other words, it is believed that the mesh and flap arrangement according to the present invention has general utility whenever a sheet or mesh must be positioned about a member not having a free end (which therefore cannot be simply inserted through an opening in the mesh) especially in a surgical repair or reinforcement.

The principles, preferred embodiments and modes of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others without departing from the spirit of the present invention and it is expressly intended that all such variations and changes which fall within the spirit and scope of the present invention as defined in the claims, may be embraced thereby.

What is claimed is:

1. A reinforcement sheet for use in surgery, said sheet having an opening defined at an interior of the sheet when the sheet is substantially flat, said sheet having a first edge which extends from the opening to the perimeter of the sheet, said sheet having a second edge with said sheet substantially overlying the first edge of said sheet when said sheet is generally flat and with said second edge substantially overlying the sheet when said sheet is generally flat, said opening being accessible from both sides of the sheet when said sheet is generally flat and when said second edge substantially overlies the sheet.

2. The reinforcement sheet of claim 1, wherein the sheet is a mesh material.

3. The reinforcement sheet of claim 2, wherein the mesh material is Marlex.

4. The reinforcement sheet of claim 1, further comprising a flap which is connected to said sheet on one side of the first edge, said flap including said second edge with said flap substantially overlying the first edge when said sheet and flap are generally flat.

5. The reinforcement sheet of claim 4, wherein the sheet includes a third edge which is substantially parallel to the first edge.

6. The reinforcement sheet of claim 5, wherein the flap is connected to said sheet substantially along the entire length of said third edge.

7. The reinforcement sheet of claim 6 wherein, said flap is substantially rectangular.

8. The reinforcement sheet of claim 4, wherein said first and third edges are oriented at an angle to one another.

9. The reinforcement sheet of claim 4, wherein said first and third edges are oriented at a right angle to one another.

10. A reinforcement sheet of mesh material for use in surgical hernia repair, said sheet having an opening to receive a body member, said opening being defined at an interior of the sheet when the sheet is substantially flat, said sheet having a first edge which extends from the opening to the perimeter of the sheet, said sheet having a second edge with said sheet substantially overlying the first edge of said sheet when said sheet is generally flat and with said second edge substantially overlying the sheet when said sheet is generally flat, said opening being accessible from both sides of the sheet when said sheet is generally flat and when said second edge substantially overlies the sheet.

11. The reinforcement sheet of claim 10, wherein the sheet is substantially rectangular.

12. The reinforcement sheet of claim 11, wherein the mesh material is Marlex.

13. The reinforcement sheet of claim 11 wherein the opening is of a predetermined size to receive the spermatic cord of the patient.

14. The reinforcement sheet of claim 11 wherein the opening is of a predetermined size to receive the round ligament of the patient.

15. The reinforcement sheet of claim 10, further comprising a flap which is connected to said sheet on one side of the first edge, said flap including said second edge with said flap substantially overlying the first edge when said sheet and said flap are generally flat.

16. The reinforcement sheet of claim 15, wherein the sheet includes a third edge which is substantially parallel to the first edge.

17. The reinforcement sheet of claim 16, wherein the flap is connected to said sheet substantially along the entire length of said third edge.

18. The reinforcement sheet of claim 17 wherein, said flap is substantially rectangular.

19. The reinforcement sheet of claim 15, wherein said first and third edges are oriented at an angle to one another.

20. The reinforcement sheet of claim 15, wherein said first and third edges are oriented at a right angle to one another.

21. A reinforcement sheet for use in surgery, said sheet being of a mesh material and having an opening defined at an interior of the sheet when the sheet is substantially flat, said sheet having a first edge which extends from the opening to the perimeter of the sheet, said sheet having a flap which is connected to said sheet on one side of the first edge, said flap defining a second edge, said flap substantially overlying the first edge when said sheet and flap are generally flat and with said second edge substantially overlying the sheet when said sheet is generally flat, said flap not overlying said opening when said sheet and said flap are generally flat.

22. The reinforcement sheet of claim 21, wherein the mesh material is Marlex.

23. The reinforcement sheet of claim 21, wherein the flap is connected to said sheet substantially along the entire length of said third edge.

24. The reinforcement sheet of claim 23, wherein the sheet includes a third edge which is substantially parallel to the first edge.

25. The reinforcement sheet of claim 23, wherein said flap is substantially rectangular.

26. The reinforcement sheet of claim 23, wherein said first and third edges are oriented at an angle to one another.

27. The reinforcement sheet of claim 23, wherein said first and third edges are oriented at a right angle to one another.

* * * * *